United States Patent
Takada et al.

(10) Patent No.: US 6,544,498 B1
(45) Date of Patent: Apr. 8, 2003

(54) PERIODONTAL DISEASE PREVENTIVE AND AMELIORATIVE AGENT

(75) Inventors: Yukihiro Takada, Kawagoe (JP); Seiichirou Aoe, Sayama (JP); Atsusi Serizawa, Kawagoe (JP); Toshiaki Suguri, Tokyo (JP); Shunichi Dousako, Urawa (JP)

(73) Assignee: Snow Brand Milk Products Co., Ltd., Hokkai-do (JP)

( * ) Notice: Subject to any disclaimer, the term of this patent is extended or adjusted under 35 U.S.C. 154(b) by 0 days.

(21) Appl. No.: 09/446,279

(22) PCT Filed: Apr. 27, 1999

(86) PCT No.: PCT/JP99/02223

§ 371 (c)(1),
(2), (4) Date: Mar. 20, 2000

(87) PCT Pub. No.: WO99/56762

PCT Pub. Date: Nov. 11, 1999

(30) Foreign Application Priority Data

Apr. 30, 1998 (JP) .............................. 10-134243

(51) Int. Cl.$^7$ .............................. A61K 7/16; A61K 38/00
(52) U.S. Cl. .............................. 424/49; 514/12; 514/16; 514/21; 514/900; 514/901
(58) Field of Search ................................ 514/12, 16, 21

(56) References Cited

U.S. PATENT DOCUMENTS

| 5,008,120 | A | | 4/1991 | Tanaka et al. |
| 5,221,734 | A | * | 6/1993 | Burk et al. .................. 530/399 |
| 5,453,284 | A | | 9/1995 | Pellico |
| 5,607,681 | A | | 3/1997 | Galley et al. |
| 5,885,964 | A | * | 3/1999 | Yamamura et al. ............ 514/12 |
| 5,976,597 | A | * | 11/1999 | Takada et al. ............... 426/491 |

FOREIGN PATENT DOCUMENTS

| EP | 0 786 473 A2 | * | 7/1997 |
| JP | 8-151331 | | 6/1996 |

* cited by examiner

Primary Examiner—Shep K. Rose
Assistant Examiner—Donna Jagoe
(74) Attorney, Agent, or Firm—Knobbe, Martens, Olson & Bear LLP

(57) ABSTRACT

A periodontal disease preventive and ameliorative agent with milk-derived basic protein as its effective ingredient, which protein is obtained by contacting a milk or milk-derived ingredient with cation-exchange resin, and then eluting a fraction adsorbed by the resin using an elution solution and which protein has an isoelectric point within a range of 7.5~11, and food/drink and a medicament such as toothpaste and gargling agents, which contain this periodontal disease preventive and ameliorative agent.

4 Claims, No Drawings

PERIODONTAL DISEASE PREVENTIVE AND AMELIORATIVE AGENT

The application claims the priority of PCT International Application No. PCT/JP99/02223, filed Apr. 27, 1999 and Japanese patent document No. 10-134243, filed Apr. 30, 1998, the disclosure of which is expressly incorporated by reference herein.

TECHNICAL FIELD

This invention relates to a periodontal disease preventive and ameliorative agent with a milk-derived basic protein as an effective ingredient. This invention also relates to the utilization of the periodontal disease preventive and ameliorative agent with a milk-derived basic protein as an effective ingredient for a food/drink and medicament.

BACKGROUND ART

In recent years, periodontal disease has become an object of public concern. Unlike dental caries, periodontal disease is a disease wherein the foundation of the teeth becomes weak and the use of teeth other than a decayed tooth is eventually lost. In addition, it is said that there are a large number of people who show symptoms of periodontal disease. In this sense, periodontal disease is a more serious disease than dental caries.

Conventionally, prevention of periodontal disease is conducted from a point of view to prevent bacteria, the cause of the disease, from propagating by removing dental plaque, or gargling with a mouthwash that contains antibacterial agent. But the effectiveness of these methods is considered to be low for advanced cases of periodontal disease. In other words, at the terminal stage of periodontal disease, a decrease in alveolar bone is observed and once alveolar bone is lost, it is difficult to reproduce it. Thus, if a tooth is lost due to periodontal disease, it interferes with people's daily life, because, needless to say, it is difficult to eat and it engenders pain, etc. Therefore, an immediate and effective preventive/ameliorative means is called for. However, at this moment, no periodontal disease preventive and ameliorative agent, which is effective to curb decrease in alveolar bone, is available.

DISCLOSURE OF INVENTION

A problem that this invention is intended to solve is to provide a periodontal disease preventive and ameliorative agent with a milk-derived basic protein as an effective ingredient. Another problem that this invention is intended to solve is to provide a medicament and food/drink in which this periodontal disease preventive and ameliorative agent with a milk-derived basic protein as an effective ingredient is contained.

The inventors of this invention discovered that basic protein, which is contained in milk in a very small amount, has a remarkable effect on the prevention and amelioration of periodontal disease and came to complete this invention.

As ingredients, milk such as cow's milk, goat's milk and sheep's milk can be used. The above-mentioned different types of milk can be used as is, in the form of fresh milk, or in the form of prepared products such as powered milk, skim milk, reduced milk, whey, etc.

The basic protein used in this invention is obtained by contacting the above-mentioned milk with cation-exchange resin, and then eluting a fraction adsorbed by the resin using an elution solution with a salt concentration of 0.1M~1.0M.

Further, the basic protein obtained can be used after desalting or condensing it, if necessary.

Basic protein obtained in this way is a milk-derived basic protein fraction that has a molecular weight distribution of 3,000~80,000 Daltons by sodium dodecylpolyacrylamide gel sulfate (SDS-PAGE) electrophoresis and has an isoelectric point of 7.5~11. Its main components are lactoferrin and lactoperoxidase and, as its amino acid constituent in protein, it contains basic amino acids by more than 15 weight percents.

In addition, the periodontal disease preventive and ameliorative agent of this invention has the above-mentioned basic protein as its main ingredient, and it can be blended into a food/drink and medicament, for example, in the form of toothpaste, gargling agents, candies, chewing gum, lozenges, etc. As a method of dosing as a medicament, it is desirable to apply about 1~50 mg/day for an adult to the surface of teeth, divided into several applications.

Further, the basic protein of this invention is essentially the ingredient of milk and is considered to be safe. In fact, as the result of toxicity tests using rats, no acute toxicity was found.

BEST MODE FOR CARRYING OUT THE INVENTION

MANUFACTURING EXAMPLE

Preparation of Milk-derived Basic Protein

After fully rinsing out a column in which 100 g of cation-exchange resin (sulfonated chitopearl manufactured by Fujibouseki) was placed using deionized water, unsterilized skim milk 101 was run through the column at a flow of 10 ml/min. After fully rinsing out the column with deionized water, 0.05M phosphate buffer (pH7) 21 containing 0.1M sodium chloride was run through. Subsequently, gradient elution from 0.5M to 1.0M was performed using 0.05M phosphate buffer (pH7) containing 0.1M sodium chloride and 0.05M phosphate buffer (pH7) containing 1.0M sodium chloride to elute basic protein adsorbed by the resin and recover it. This eluate was desalted using a reverse osmosis membrane. After concentrating it, it was lyophilized, and powdered basic protein was obtained. By repeating this operation eight times and 821 g of basic protein was obtained.

TESTING EXAMPLE

Evaluation of Decreased Alveolar Bone 54 six-week-old golden hamsters were raised preliminary for a week. Under etherization, sterilized silk suture No. 4 for surgical use was put 5 times around the tooth cervix part of M1 of the golden hamsters. They were raised by being fed food (D#2000: Keyes, P. H. and Jordan: Archs. Oral. Biol. 9: 377–400, 1964) to cause them to have periodontal disease. The hamsters were then divided into three equal groups of 18 each, the control group, the basic protein 0.5 mg/ml group and the basic protein 5 mg/ml group. Treatment to continuously soak the inside of oral cavity of the hamsters with basic protein of respective concentration for about 10 minutes twice a day was conducted. Three days, seven days and fourteen days after the start of this treatment, by selecting six hamsters from each group, after performing fixed perfusion using 2.5% glutaraldehyde solution (pH 7.4) for about 20 minutes, both sides of the lower jaw bone were removed and the amount of decreased alveolar bone was evaluated. After the removed jawbones were fixed with 2.5% glutaraldehyde solution, a soft X-ray photograph was taken. The photos were analyzed using an image analyzer (PIAS LA-555). By measuring an area between an enamel cement border and the alveolar bone top near M1, the amount of decreased alveolar bone was evaluated.

The results are shown in Table 1. The amount of decreased alveolar bone of the hamsters in the groups to which basic protein 0.5 mg/ml and 5 mg/ml were administered is significantly low and this effect was concentration-dependent. These results demonstrate that milk-derived basic protein inhibits decrease in the alveolar bone and it is effective for the prevention and the amelioration of periodontal disease.

TABLE 1

The Effectiveness to Control the Decreased Alveolar Bone by Milk-derived Basic Protein

| Control | | Basic Protein | Basic Protein |
|---|---|---|---|
| | | 0.5 mg/ml | 5 mg/ml |
| Decreased Area (mm$^2$) | | | |
| 3 days after | 0.25 | 0.22 | 0.14 |
| 7 days | 1.21 | 0.83** | 0.36** |
| 14 days | 1.64 | 1.01** | 0.45** |

**Note: As contrasted with the control group, there are significant differences. (P < 0.01)

EXAMPLE 1
Manufacture of Toothpaste for Periodontal Disease Preventive and Ameliorative Purposes Toothpaste for periodontal disease preventive and ameliorative purposes was manufactured by blending each ingredient with the percentage shown in Table 2 below and placing the product in a container.

TABLE 2

| Glycerin | 70.0 (weight percent) |
|---|---|
| Silicon dioxide | 20.0 |
| Xanthan gum | 1.0 |
| Mint flavor | 1.0 |
| Titanium oxide | 0.7 |
| Sodium fluoride | 0.3 |
| Distilled water | 6.5 |
| Milk basic protein | 0.5 |

EXAMPLE 2
Manufacture of a Gargle for Periodontal Disease Preventive and Ameliorative Purposes A gargle for periodontal disease preventive and ameliorative purposes was manufactured by blending each ingredient in the percentage shown in Table 3.

TABLE 3

| Ethanol | 8.0 (weight percent) |
|---|---|
| Perfume | 0.9 |
| Sorbitol | 5.0 |
| Propylene glycol | 5.0 |
| Milk basic protein | 0.1 |
| Distilled water | 81.0 |

EXAMPLE 3
Manufacture of Chewing Gum for Periodontal Disease Preventive and Ameliorative Purposes According to the weight percentage shown in Table 4, after gum base was dissolved and each ingredient was blended in, the product was shaped, resulting in chewing gum for periodontal disease preventive and ameliorative purposes.

TABLE 4

| Gum base | 20.0 (weight percent) |
|---|---|
| Corn syrup | 9.0 |
| Dextrose 1 hydrate | 10.0 |
| Lactose | 5.0 |
| Glycerin | 5.0 |
| Sugar | 50.0 |
| Milk basic protein | 1.0 |

EXAMPLE 4
Manufacture of Candies for Periodontal Disease Preventive and Ameliorative Purposes Sugar and glutinous starch syrup were blended at the weight percentages shown in Table 5. The mixture was boiled at 150° C. (302° F.) until it was condensed. After it was cooled to 115° C. (239° F.), milk basic protein in the amount of 0.1 weight percent was stirred in. After it was cooled on a cooling disk, it was shaped, resulting in candies for periodontal disease preventive and ameliorative purposes.

TABLE 5

| Sugar | 69.9 (weight percent) |
|---|---|
| Glutinuos starch syrup | 30.0 |
| Milk basic protein | 0.1 |

Industrial Applicability

The periodontal disease preventive and ameliorative agent of this invention with milk-derived basic protein as its effective ingredient can inhibit alveolar bone decrease that occurs in the terminal stage of periodontal disease. Hence it greatly contributes to prevention and amelioration of this disease.

Also, since the periodontal disease preventive and ameliorative agent of this invention can be blended in a food/drink and medicament, for example, in the forms of toothpaste, gargling agents, candies, chewing gum, lozenges, etc. so as to effectively apply them to the surface of teeth, substantial preventive and ameliorative effects can be obtained.

What is claimed is:

1. A method of preventing and ameliorating a periodontal disease comprising administrating a milk-derived basic protein to a candidate for the prevention and amelioration of the periodontal disease in an effective amount to prevent and ameliorate the disease, (a) said protein having a molecular weight distribution of 3,000–80,000 and an isoelectric point within a range of 7.5–11, (b) said protein's main components being lactoferrin and lactoperoxidase, (c) said protein containing, as its amino acid constituent in protein, basic amino acids by more than 15 weight percents, and (d) said protein being obtained by passing a milk or milk-derived ingredient through cation-exchange resin and performing gradient elution using phosphate buffer of pH 7 containing 0. 1M sodium chloride and phosphate buffer of pH 7 containing 1.0M sodium chloride.

2. A method of preventing and ameliorating a periodontal disease comprising providing to a candidate for the prevention and amelioration of the periodontal disease a food and drink comprising a milk-derived basic protein as its effective ingredient, (a) said protein having a molecular weight distribution of 3,000–80,000 and an isoelectric point within a range of 7.5–11, (b) said protein's main components being lactoferrin and lactoperoxidase, (c) said protein containing, as its amino acid constituent in protein, basic amino acids by more than 15 weight percents, and (d) said protein being obtained by passing a milk or milk-derived ingredient through cation-exchange resin and performing gradient elution using phosphate buffer of pH 7 containing 0.1M sodium chloride and phosphate buffer of pH 7 containing 1.0M sodium chloride.

3. A method of preventing and ameliorating a periodontal disease comprising providing to a candidate for the prevention and amelioration of the periodontal disease a medicament comprising a milk-derived basic protein as its effective ingredient, (a) said protein having a molecular weight distribution of 3,000–80,000 and an isoelectric point within a range of 7.5–11, (b) said protein's main components being lactoferrin and lactoperoxidase, (c) said protein containing, as its amino acid constituent in protein, basic amino acids by more than 15 weight percents, and (d) said protein being obtained by passing a milk or milk-derived ingredient through cation-exchange resin and performing gradient elution using phosphate buffer of pH 7 containing 0.1M sodium chloride and phosphate buffer of pH 7 containing 1.0M sodium chloride.

4. A method of preventing and ameliorating a periodontal disease comprising providing to a candidate for the prevention and amelioration of the periodontal disease a toothpaste or gargles comprising a milk-derived basic protein as its effective ingredient, (a) said protein having a molecular weight distribution of 3,000–80,000 and an isoelectric point within a range of 7.5–11, (b) said protein's main components being lactoferrin and lactoperoxidase, (c) said protein containing, as its amino acid constituent in protein, basic amino acids by more than 15 weight percents, and (d) said protein being obtained by passing a milk or milk-derived ingredient through cation-exchange resin and performing gradient elution using phosphate buffer of pH 7 containing 0.1M sodium chloride and phosphate buffer of pH 7 containing 1.0M sodium chloride.

* * * * *